US010149872B2

(12) United States Patent
Espadaler Mazo et al.

(10) Patent No.: US 10,149,872 B2
(45) Date of Patent: Dec. 11, 2018

(54) STRAIN OF *LACTOBACILLUS PENTOSUS* AS PROBIOTIC

(71) Applicant: GYNEA LABORATORIOS, S.L., Palau-Solita I Plegamans (ES)

(72) Inventors: Jordi Espadaler Mazo, Girona (ES); Miguel Angel Losada Diaz, Sant Marti de Tous (ES)

(73) Assignee: Gynea Laboratorios, S.L., Palau-Solita I Plegamans (ES)

( * ) Notice: Subject to any disclaimer, the term of this patent is extended or adjusted under 35 U.S.C. 154(b) by 73 days.

(21) Appl. No.: 14/911,730

(22) PCT Filed: Aug. 11, 2014

(86) PCT No.: PCT/EP2014/067177
§ 371 (c)(1),
(2) Date: Feb. 12, 2016

(87) PCT Pub. No.: WO2015/022297
PCT Pub. Date: Feb. 19, 2015

(65) Prior Publication Data
US 2016/0193260 A1  Jul. 7, 2016

(30) Foreign Application Priority Data
Aug. 12, 2013  (EP) ..................... 13382326

(51) Int. Cl.
| | |
|---|---|
| *C12N 1/20* | (2006.01) |
| *A61K 35/747* | (2015.01) |
| *A61K 8/99* | (2017.01) |
| *A61L 15/36* | (2006.01) |
| *A61Q 17/00* | (2006.01) |
| *A61Q 19/10* | (2006.01) |
| *C12N 15/01* | (2006.01) |
| *C12R 1/225* | (2006.01) |
| *A23L 33/135* | (2016.01) |
| *A61K 35/00* | (2006.01) |

(52) U.S. Cl.
CPC .......... *A61K 35/747* (2013.01); *A23L 33/135* (2016.08); *A61K 8/99* (2013.01); *A61L 15/36* (2013.01); *A61Q 17/005* (2013.01); *A61Q 19/10* (2013.01); *C12N 15/01* (2013.01); *C12R 1/225* (2013.01); *A23V 2002/00* (2013.01); *A61K 2035/115* (2013.01); *A61K 2800/92* (2013.01)

(58) Field of Classification Search
None
See application file for complete search history.

(56) References Cited

U.S. PATENT DOCUMENTS 7,125,708 B2 * 10/2006 Wynne .................. A61K 31/65
424/93.45

FOREIGN PATENT DOCUMENTS

| EP | 1197231 A | 4/2002 |
|---|---|---|
| JP | 2008013502 | 1/2008 |
| WO | 03833681 A2 | 4/2003 |
| WO | 2012101500 A1 | 8/2012 |

OTHER PUBLICATIONS

Andreoletti, O., et al. The maintenance of the list of QPS microorganisms intentionally added to food or feed. Question No. EFSA-Q-2008-006. The EFSA Journal. 2008, vol. 923, pp. 1-48.
Anukam, K.C., et al. Clinical study comparing probiotic Lactobacillus GR-1 and RC-14 with metronidazole vaginal gel to treat symptomatic bacterial vaginosis. Microbes and Infection. 2006, vol. 8, Nos. 12-13, pp. 2772-2776.
Araya, M., et al. Guidelines for the Evaluation of Probiotics in Food—Joint FAO/WHO Working Group, FAO/WHO. Editor 2002. Food and Agriculture Organization of the United Nations and World Health Organization: Ontario, Canada.
Archibald, F., Manganese: its acquisition by and function in the lactic acid bacteria. Crit Rev Microbial, 1986, vol. 13, No. 1, pp. 63-109.
Atassi, F., et al. Lactobacillus strains isolated from the vaginal microbiota of healthy women inhibit Prevotella bivia and Gardnerella vaginalis in coculture and cell culture. FEMS Immunology & Medical Microbiology. 2006, vol. 48, No. 3, pp. 424-432.
Bories, G., et al. Update on the criteria used in the assessment of bacterial resistance to antibiotics of human or veterinary importance. The EFSA Journal. 2008, vol. 732, pp. 1-15.
Cole, J.R., et al. The Ribosomal Database Project (RDP-II): introducing myRDP space and quality controlled public data. Nucl. Acids Res. 2007, vol. 35(suppl_1), pp. D169-172.
Culici, M., et al. Adhesion of Lactobacillus plantarum p. 17630 to vaginal epithelial cells and its influence on Candida albicans adhesion. GIMMOC. 2004, vol. 8, No. 1, pp. 34-41.
Dho, G., et al. Microbial characteristics of Lactobacillus plantarum P17630 contained in vaginal suppositories. GIMMOC. 2003, vol. VII, No. 2, pp. 102-108.
Dimitonova, S.P. et al. Antimicrobial activity and protective properties of vaginal lactobacilli from healthy Bulgarian women. Anaerobe. 2007, vol. 13, No. 5-6, pp. 178-184.
Ghosh, S.K., et al. Quantification of Human beta-Defensin-2 and -3 in Body Fluids: Application for Studies of Innate Immunity. Clin Chem. 2007, vol. 53, No. 4, pp. 757-765.
Jacques, M. et al. The normal microflora of the female rabbits genital tract. Can J Vet Res. 1986, vol. 50, pp. 272-274.
Larsson, P.G., et al. Human lactobacilli as supplementation of clindamycin to patients with bacterial vaginosis reduce the recurrence rate; a 6-month, double-blind, randomized, placebo-controlled study. BMC Women's Health. 2008, vol. 8, No. 1, p. 3.

(Continued)

*Primary Examiner* — Irene Marx
(74) *Attorney, Agent, or Firm* — Cheryl H. Agris; Agris & von Natzmer, LLP

(57) ABSTRACT

Provided is the new strain *Lactobacillus pentosus* CECT 7504 and compositions and products comprising said strain and uses in the prevention and/or treatment of candidiasis (oral, intestinal and vaginal) and of bacterial vaginosis.

7 Claims, 3 Drawing Sheets
Specification includes a Sequence Listing.

(56) References Cited

OTHER PUBLICATIONS

Martinez, R.C.R., et al. Improved treatment of vulvovaginal candidiasis with fluconazole plus probiotic Lactobacillus rhamnosus GR-1 and Lactobacillus reuteri RC-14. Letters in Applied Microbiology. 2009, vol. 48, No. 3, pp. 269-274.

Mastromarino, P., et al. Characterization and selection of vaginal Lactobacillus strains for the preparation of vaginal tablets. Journal of Applied Microbiology. 2002, vol. 93, No. 5, pp. 884-893.

Okkers, D. J. et al. Characterization of pentocin TV35b, a bacteriocin-like peptide isolated from Lactobacillus pentosus with a fungistatic effect on Candida albicans. Journal of Applied Microbiology. 1999, vol. 87, No. 5, pp. 726-734.

Owen, D.H. et al. A vaginal fluid simulant. Contraception. 1999, vol. 59, No. 2, pp. 91-95.

Pascual, L.M. et al. Lactobacillus rhamnosus L60, a potential probiotic isolated from the human vagina. Journal of General and Applied Microbiology. 2008, vol. 54, No. 3, pp. 141-148.

Richter, S.S., et al. Antifungal Susceptibilities of Candida Species Causing Vulvovaginitis and Epidemiology of Recurrent Cases. J. Clin. Microbial. 2005, vol. 43, No. 5, pp. 2155-2162.

Rodas, A.M., et al. Polyphasic study of wine Lactobacillus strains: taxonomic implications. Int J Syst Evol Microbiol. 2005, vol. 55, No. 1, pp. 197-207.

Saarela, M., et al. Stationary-phase acid and heat treatments for improvement of the viability of probiotic lactobacilli and bifidobacteria. Journal of Applied Microbiology. 2004, vol. 96, No. 6, pp. 1205-1214.

Stapleton A.E, et al. Randomized, Placebo-Controlled Phase 2 Trial of a Lactobacillus crispatus Probiotic Given Intravaginally for Prevention of Recurrent Urinary Tract Infection, Clinical Infectious Diseases. 2011, vol. 52, No. 10, pp. 1212-1217.

Valore, E.V., et al. Reversible Deficiency of Antimicrobial Polypeptides in Bacterial Vaginosis. Infect. Immun. 2006, vol. 74, No. 10, pp. 5693-5702.

Wang, Q., et al. Naive Bayesian Classifier for Rapid Assignment of rRNA Sequences into the New Bacterial Taxonomy. Appl. Environ. Microbial. 2007, vol. 73, No. 16, pp. 5261-5267.

International Preliminary Report on Patentability for PCT/EP2014/067177, dated Feb. 16, 2016.

International Search Report and Written Opinion for PCT/EP2014/067177, dated Dec. 1, 2014.

AU Appln. No. 2014307938, Notice of Acceptance, dated Aug. 16, 2017.

Response to AU Office Action in AU Appln. No. 2014307938 dated Aug. 2, 2017.

Response to EP Office Action in EP Appln. No. 14757862.9 (published as EP3035943A1) dated Sep. 27, 2016.

AU Office Action in AU Appln. No. 2014307938 dated Aug. 28, 2016.

1. http://www.ab-biotics.com:80/EN/15/menu/nutriceuticals.html, dated Oct. 8, 2010 (retrieved from wayback.org).

2. http://www.ab-biotics.com:80/products/areas.html, dated Nov. 8, 2016 (retrieved from wayback.org).

\* cited by examiner

STRAIN OF *LACTOBACILLUS PENTOSUS* AS PROBIOTIC

The present invention relates to the fields of medicine, microbiology and food technology and particularly, to a novel strain of *Lactobacillus pentosus* to be used as a probiotic to benefit human health.

BACKGROUND ART

Probiotics

The concept of probiotic microorganisms was born from the hypothesis of the Nobel Prize Elie Metchnikoff, who suggested that the consumption of bacteria able to produce fermentation (*Lactobacillus*) has a positive effect on the microbiota of the colon, reducing the presence of bacterial toxins and other microbial activities which have a negative impact on human health.

"Probiotics are live microorganisms that after its administration engaged in the consumer more benefits than basic nutritional natural". Nowadays, there are a lot of references about the usefulness of probiotics to treat several disorders of gastrointestinal health, as well as studies that suggest its utility to activate the immune system and prevent allergies.

Probiotic bacteria must fulfil several requirements related to lack of toxicity, viability, adhesion and beneficial effects. The properties of each bacterial strain are unique and cannot be extrapolated to other strains of the same species (Araya, M., et al. Guidelines for the Evaluation of Probiotics in Food—Joint FAO/WHO Working Group. FAO/WHO. Editor 2002. Food and Agriculture Organization of the United Nations and World Health Organization: Ontario, Canada). Therefore, it is important to find those strains that have a better performance in all probiotic requirements.

Although the concept of probiotics was associated with intestinal microbial flora, studies conducted as early as 1988 showed that this concept could also be extended to the vaginal flora of women. A few scientific groups have been developing this idea for some years, which culminated in the identification of some strains of *Lactobacillus* which are useful to treat complications of vaginal health (Anukam, K. C., et al. Clinical study comparing probiotic *Lactobacillus* GR-1 and RC-14 with metronidazole vaginal gel to treat symptomatic bacterial vaginosis. *Microbes and Infection.* 2006, Vol. 8, Nos. 12-13, pages 2772-2776; Larsson, P. G., et al. Human lactobacilli as supplementation of clindamycin to patients with bacterial vaginosis reduce the recurrence rate; a 6-month, double-blind, randomized, placebo-controlled study. *BMC Women's Health.* 2008, Vol. 8, No. 1, page 3), thus demonstrating the concept of probiotic for vaginal health.

Healthy Vaginal Flora

The appearance of vaginal secretions and itching are the most common causes of gynaecological visits. This may be due to allergic reactions, contact with irritant agents (cloth fibber, soap, spray, etc.) or in many cases due to an infection.

The healthy vaginal flora is mostly composed of *Lactobacilli*, which maintain the natural acidic pH of the vagina (between 3.9 and 4.3), preventing its colonization by other microorganisms. When this natural flora is weakened, e.g. by systemic antibiotic treatments, infection by pathogenic species becomes much more likely. The most frequent complications of healthy vaginal flora are vulvovaginal candidiasis and bacterial vaginosis.

Vulvovaginal Candidiasis

*Candida* is a highly prevalent yeast that can be found in small numbers in the vaginal flora without any symptoms of disease. Symptoms appear when vaginal flora equilibrium is disturbed and the population of *Candida* increases compared to the amount of protective *Lactobacilli*. Typical symptoms of *Candida* infection include vaginal itching and burning, as well as dyspareunia and vaginism. Approximately, the 75% of the cases of the vulvovaginal candidiasis are due to *Candida albicans*, and an additional 15% are due to *Candida glabrata* (Richter, S. S., et al. Antifungal Susceptibilities of *Candida* Species Causing Vulvovaginitis and Epidemiology of Recurrent Cases. *J. Clin. Microbiol.* 2005, Vol. 43, No. 5, pages 2155-2162). It is estimated that 75% of women experience at least one episode in the course of their lifetime. Moreover, 25% of the cases are recurrent with four or more episodes per year.

Infection often occurs after treatment with antibiotic therapy prescribed with a different therapeutic aim. It is also common in women taking oral contraceptives containing estrogens, in pregnant women and in women with diabetes. *Candida* infections are treated with antimycotics, such as triazole drugs (e.g. fluconazole, clotrimazole, myconazole, itraconazole) or nystatin. However, it is noteworthy that strains of *Candida glabrata* tend to display a high resistance against such treatments, while up to 20% of the strains of *Candida albicans* isolated in clinics present resistance to fluconazole, one of the most typical treatments, stressing out the importance of finding new therapeutic tools for the management of vulvovaginal candidiasis.

In addition to its acidic pH, vaginal fluid contains several antimicrobial proteins, such as lysozyme, defensins and lactoferrin. During vulvovaginal candidiasis the concentration of these substances increases beyond the normal levels in approximately 25% of women (Valore, E. V., et al. Reversible Deficiency of Antimicrobial Polypeptides in Bacterial Vaginosis. *Infect. Immun.* 2006, Vol. 74, No. 10, pages 5693-5702). This response is usually insufficient to ward off yeasts such as *Candida*, as the effect of these substances is more bacteriostatic or bactericidal than antimycotic. However, since the healthy vaginal flora is mostly composed of bacteria of the *Lactobacillus* genus this abnormal increase in antimicrobial proteins can contribute to further delay the recuperation of the healthy flora of the vagina. Moreover, this stresses out the need of considering the resistance to these antimicrobial factors when searching for *Lactobacilli* suitable to be used as probiotics.

Bacterial Vaginosis

Bacterial vaginosis is caused by an overgrowth of bacterial species usually absent in the vaginal flora or found in very small amounts. The most common species are *Gardnerella vaginalis* and *Atopobium vaginale*, but a precise aetiological agent has not been found so far. About 1 out of 5 women will develop bacterial vaginosis along an interval between 6 and 12 months. Although bacterial vaginosis can cause unusual vaginal discharges and fishy odour, most cases are asymptomatic. A typical trait of bacterial vaginosis is the rise of the pH above 4.5, due to the disappearance of *Lactobacilli*, which further facilitates the growth of other bacterial species.

Bacterial vaginosis is treated with antibiotics, such as metronidazole and clindamicyn. However, bacterial vaginosis displays a high recurrence rate, up to 35% during the first month and up to 70% during the first year. It has also been observed that the antibiotic treatment of vaginosis can lead to vulvovaginal candidiasis as a secondary infection, since antibiotics, especially clindamicyn, also affect *Lactobacilli*.

Also, it has been shown that women that have bacterial vaginosis tend to have premature babies or babies with low weight—less than 2.5 kg —. Sometimes the infection can spread to the fallopian tubes. This type of infection is called pelvic inflammatory disease (PID) and can cause infertility and damage to the fallopian tubes, increasing the risk of ectopic pregnancy. Bacterial vaginosis also increases the risk of urinary tract infections and sexually transmitted diseases.

Probiotics for the Management of Vulvovaginal Candidiasis and Bacterial Vaginosis There are currently several probiotic strains marketed to help manage vulvovaginal candidiasis, such as *Lactobacillus rhamnosus* GR1, *Lactobacillus fermentum* RC14, *Lactobacillus plantarum* P17630 and *Lactobacillus acidophilus* NAS. However, none of them has been tested for their ability to withstand the elevated concentrations of antimicrobial factors that occur in approximately 1 out of 4 cases of infection. Plus, there is only one probiotic solution (BION Flore Intime®, composed by strains *Lactobacillus rhamnosus* GR1 and *Lactobacillus reuteri* RC14) for the management of vulvovaginal candidiasis whose efficacy claims are supported by a randomized placebo-controlled clinical trial (Martinez, R. C. R., et al. Improved treatment of vulvovaginal candidiasis with fluconazole plus probiotic *Lactobacillus rhamnosus* GR-1 and *Lactobacillus reuteri* RC-14. *Letters in Applied Microbiology.* 2009, Vol. 48, No. 3, pages 269-274).

On the other hand, there are two probiotic products for the management of bacterial vaginosis whose health claims are supported by randomised placebo-controlled, clinical trials: BION Flore Intime®—*Lactobacillus rhamnosus* GR1 and *Lactobacillus fermentum* RC14—and EcoVag®—*Lactobacillus gasseri* DSM 14869 and *Lactobacillus rhamnosus* DSM 14870 (Anukam, K. C., et al. 2006, supra; Larsson, P. G., et al. 2008, supra).

The art describes other strains as potential vaginal probiotics, such as EP1436380 B1, which describes the strain *Lactobacillus pentosus* NCIMB 41114 isolated from a fecal culture obtained from a healthy adult individual and cultured in the presence of tetracycline. The document describes that due to its ability of suppressing the growth of *Candida* species and that the strain is resistant to tetracycline and related antibiotics, it can be useful to combat undesirable growth of *Candida* in any region of the body, in particular in Irritable Bowel Syndrome. This document is silent about the inhibitory activity of the strain against *Candida glabrata*, nor demonstrates the ability of the strain to adhere to the vaginal epithelium and survive in the vaginal environment or to resist to antimicrobial substances present in it, such as lysozyme.

Okkers, D. J. et al. 1999 describes that strain *Lactobacillus pentosus* TV35b, isolated from the posterior fornix secretions of the vagina of a prenatal patient, produced a bacteriocin-like peptide (pentocin TV35b), which is inhibitory to *Candida albicans* and some bacterial species. The document is silent about the inhibitory activity of the strains against *Candida glabrata* (Okkers, D. J. et al. Characterization of pentocin TV35b, a bacteriocin-like peptide isolated from *Lactobacillus pentosus* with a fungistatic effect on *Candida albicans*, *Journal of Applied Microbiology.* 1999, Vol. 87, No. 5, pages 726-734).

On the other hand, the art describes vaginal strains which do not present inhibitory activity against *Candida albicans*. For instance, in Dimitonova et al. 2007, the inhibitory activity of 20 strains of *Lactobacilli*, isolated from vaginal swabs of healthy Bulgarian women, was assessed. None of the 20 strains inhibited the growth of *Candida albicans* (Dimitonova, S. P. et al. Antimicrobial activity and protective properties of vaginal *lactobacilli* from healthy Bulgarian women. *Anaerobe.* 2007, Vol. 13, No. 5-6, pages 178-184).

The art also teaches that presence of inhibitory activity against *Candida albicans*, does not mean that the bacterial strain is also antagonist against *Candida glabrata*. For instance, in Pascual L. M. et al. 2008 a strain of *Lactobacillus* isolated from the vagina of nonpregnant, healthy, premenopausal women was identified as *Lactobacillus rhamnosus* L60. *Lactobacillus rhamnosus* L60 displayed a wide spectrum of antimicrobial activity against urogenital pathogens, and resistance to antibiotics commonly prescribed for infections caused by these pathogens. This strain was antagonist against 10 strains of *Candida albicans* but was not antagonist against the 3 strains of *Candida glabrata* tested [Pascual, L. M. et al. *Lactobacillus rhamnosus* L60, a potential probiotic isolated from the human vagina. *Journal of General and Applied Microbiology.* 2008, Vol. 54, No. 3, pages 141-148).

Therefore, the fact that the described *Lactobacilli* for use as potential vaginal probiotic are isolated from vagina does not mean that they present inhibitory activity against species of *Candida*. Moreover, the fact that a strain of *Lactobacillus* is antagonist against *Candida albicans* does not mean that also possess activity against other species of *Candida*, such as *Candida glabrata*. Thus, being antagonist for *Candida* species is not an inherent feature of *Lactobacilli*.

WO 2012/101500 A1 describes an effervescent composition in solid form for use in vaginal applications for the treatment of vaginal infections. The effervescent composition comprises among galenic components, a probiotic bacterial strain for reducing and/or eliminating the presence of pathogenic agents in the vaginal environment. The strain is selected from a long list of the most common species used as probiotics, from *Lactobacillus* and *Bifidobacterium* genus. The document does not include a test to evaluate the properties of the strains. The invention is focused in the galenic composition designed to enhance the survival of the probiotics during their manufacture and to improve administration. The strains mentioned in the document are commercially available and the pathogens mentioned are common in vaginal pathologies.

JP 2008013502 A describes the use of a product obtained by a fermentation process of a cruciferous plant, such as e.g. broccoli, with lactic acid bacteria such as *Lactobacillus pentosus*, to treat or prevent *Candida* infections like vaginitis. Tests are done with *Candida albicans* deposited strains. The document is silent about the inhibitory activity of the fermented product against *Candida glabrata*.

On the other hand, as explained above, antibacterial substances in vaginal fluid are increased beyond normal levels in approximately 25% of women experiencing vulvovaginal candidiasis. These substances have a significant inhibitory effect on *Lactobacilli*. A few *Lactobacilli* are currently used as vaginal probiotics; however none of them has been tested for the capacity to survive in the conditions where antimicrobial factors are increased in vaginal fluid. Moreover, none of the current vaginal probiotics has been tested for its activity specifically against *Candida glabrata*. *C. glabrata* accounts for a significant fraction of *Candida* infections and displays a higher resistance to current antimycotic treatments, thus presenting a greater therapeutic challenge.

SUMMARY OF THE INVENTION

The inventors provide a new strain of *Lactobacillus pentosus* suitable as a probiotic for the management of vaginal infections, as a result of extensive studies of different *Lactobacilli* strains isolated from healthy humans. Strain 11001 was isolated from the vaginal flora of a healthy young woman living under poor hygienic conditions. The strain of *Lactobacillus pentosus* was deposited on 6 Mar. 2009 in the Spanish Type Culture Collection (Colección Española de Cultivos Tipo, CECT, Edificio 3 CUE, Parc Cientific, Universitat de València, Catedrático Agustin Escardino, 9, 46980-Paterna, Valencia, Spain), by the depositor AB-Biotics, S.A., sited at Edifici Eureka, office P1M1.1, Campus UAB, 08193-Bellaterra (Spain). The strain of *L. pentosus* was received the accession number CECT 7504 after the International Authority of Deposit declared the strain as viable.

The depositor AB-Biotics, S.A. authorized the Applicant, GYNEA Laboratorios S.L., to refer to the aforementioned deposited biological material in the European patent application having the representative's reference number P2723EP00 or in any subsequent patent application derived from it or claiming priority from it, and gave his unreserved and irrevocable consent to the deposited material being made available to the public in accordance with Rule 33 EPC as from the date of filing of the aforementioned patent application.

The strain CECT 7504 was selected among 100 isolated *Lactobacilli* strains because of the following distinguishing properties:

High survival to the antimicrobial factors found in vaginal fluid, especially lysozyme. As explained above, these factors are often increased in a subset of patients with candidiasis (approximately 25% of cases), and could be very harmful to many probiotics. As indicated in the examples section, only a fraction of the *Lactobacilli* of vaginal origin can survive to the increased concentrations of lysozyme which can be found in patients with vulvovaginal candidiasis but not in healthy patients (see EXAMPLE 3 below, where 10 strains of *Lactobacillus* are tested). This means that resistance to these proteins is not an inherent feature of *Lactobacilli*. Moreover, it is believed that no prior art describes vaginal probiotics with capacity to survive in the conditions where the concentration of natural antimicrobial factors is increased in the vaginal fluid. So, known probiotics would not be effective for this subset of patients. Surprisingly, the strain CECT 7504 showed a marked resistance to these conditions, thus being especially indicated for this subset of patients. Particularly, strain CECT 7504 showed a high resistance to lysozyme concentrations up to 16 mg/l (see FIG. 2). Lysozyme is the antimicrobial factor found in the highest concentration in the vaginal fluid besides organic acids, and the one whose activity is most directed against Gram-positive organisms, such as *Lactobacilli*. On the other hand, the commercial strain *L. plantarum* P17630 (ISADIN) showed a marked decrease in viability (90%) when exposed to concentrations of lysozyme above 4 mg/l, such as the ones that can be found in some vulvovaginal candidiasis patients.

The capacity to inhibit the growth of both *C. albicans* and *C. glabrata*, thus displaying a broader spectrum activity to help manage *Candida* infections such as vulvovaginal candidiasis. As indicated in the background art and the examples section, some *Lactobacilli* of vaginal origin display significant antagonistic activity against one or two *Candida* isolates, but only a small fraction displays a significant activity against a panel of several isolates of both *Candida albicans* and *Candida glabrata* species (see EXAMPLE 4). Thus, as mentioned above, the capacity of inhibiting *Candida* isolates is not an inherent feature of *Lactobacilli*. Surprisingly, strain CECT 7504 showed higher activity against the three strains of *C. albicans* tested when compared to the commercial probiotic strain *Lactobacillus plantarum* P17630, and also showed high activity against one strain of *C. glabrata* and some activity against a different *C. glabrata* strain, while both *L. plantarum* P17630 and other wild-type strains showed low activity against the former strain and no activity against the latter strain of *C. glabrata* (TABLE 3).

The capacity to survive against high concentrations of antimycotic agents typically used to manage *Candida* infections, thus allowing the bacterial strain of the present invention to be co-administered with said antimycotic agents.

An improved capacity to acidify vaginal fluid compared to other isolates and commercial control, thus displaying a high potential to help manage bacterial vaginosis. The ability to acidify the vaginal fluid is often extrapolated from the ability to acidify typical laboratory culture media or milk. However, the composition of the vaginal fluid (low concentration of nutrients) is quite different from the composition of laboratory media or milk, which are nutrient-rich. Instead, the strain of the invention has been tested in a medium simulating the real composition of vaginal fluid.

The ability to strongly adhere to vaginal epithelial cells.

A good growth in industrial medium.

Good tolerability when tested in an animal model of vaginal irritation.

Good tolerability and colonization capacity when tested in human volunteers.

In summary, it is believed that no prior art describes a *Lactobacillus* strain and particularly a *Lactobacillus pentosus* strain with the above-mentioned features. The art describes other *Lactobacillus* strains particularly good for one of said features, but what is noteworthy is that the strain of *Lactobacillus pentosus* CECT 7504 meets all such qualities together. Further to meet the above-mentioned key features for the management of vaginal infections, the strain of the invention also presents good probiotic features related to lack of toxicity, viability, adhesion and beneficial effects. The examples bellow provide (by way of example) protocols to determine each one of the probiotic features and it is also demonstrated that strain CECT 7504 has excellent probiotic features.

Thus, in a first aspect the present invention provides a composition comprising an effective amount of *Lactobacillus pentosus* CECT 7504. The term "effective amount" as used herein, means an amount agent high enough to deliver the desired benefit, but low enough to avoid serious side effects within the scope of medical judgment.

A wide variety of lactic acid bacterial species have a long history of apparent safe use. The European Food Safety Authority has developed a system granting the "Qualified Presumption of Safety" (QPS) status to taxonomical units with a proven long history of apparent safe use. Strain CECT 7504 belongs to a bacterial species that has QPS status (Andreoletti, O., et al. The maintenance of the list of QPS microorganisms intentionally added to food or feed. Question no: EFSA-Q-2008-006; *The EFSA Journal*. 2008, Vol. 923, pages 1-48).

The emergence and spread of resistance to antimicrobials in bacteria pose a threat to human and animal health and represent a major financial and societal cost. When resistance to an antimicrobial agent is inherent to a bacterial species, it is generally referred to as 'intrinsic resistance' (sometimes called 'natural resistance'). Intrinsic resistance is presumed to present a minimal potential for horizontal spread, whereas acquired resistance mediated by added genes is considered as having a high potential for lateral spread. The inventors of the present invention have found that the strain forming the composition of the invention does not display any significant resistance to antibiotics of human and/or veterinary importance (ampicillin, gentamicin, streptomycin, erythromycin, tetracycline, clindamycin, and chloramphenicol) according to the guidelines of the European Food Safety Authority (Bories, G. et al. Update on the criteria used in the assessment of bacterial resistance to antibiotics of human or veterinary importance. *The EFSA Journal.* 2008, Vol. 732, pages 1-15), thus precluding the risk of a potential transfer of antibiotic resistance to pathogenic species.

In another aspect, the invention provides a composition comprising an effective amount of the strain of the invention, for use as a pharmaceutical product, a medicament, a food product, an edible product, a food supplement, a medical food, or a personal hygiene product.

As said above, strain CECT 7504 displays a significant activity against *Candida* species. Therefore, in a third aspect, the invention provides the composition as defined above for use in the prevention and/or treatment of candidiasis. This aspect can be alternatively formulated as the use of a composition as defined in the first aspect of the invention for the manufacture of a pharmaceutical product, a medicament, a food product, an edible product, a food supplement, a medical food, or a personal hygiene product for the prevention and/or treatment of candidiasis. This may be also alternatively formulated as a method for the prevention and/or treatment of candidiasis in a human, comprising administering to said human in need thereof an effective amount of the composition as defined in the first aspect of the invention.

The composition of the invention is particularly useful for the prophylactic treatment of individuals susceptible to candidiasis and also for the therapeutic management of individuals infected with microorganisms of the genus *Candida*. Particularly, the composition of the invention can be administered to infants, children, and AIDS patients to prevent or treat thrush (oral candidiasis) or *Candida* diaper rash. Further, AIDS patients would benefit from the composition disclosed herein as the likelihood of acquiring a *Candida* infection would be decreased, and if acquired, would experience less translocation of *Candida* when orally ingested. The composition is also useful to prevent infections endangering the foetus in pregnant women, preterm labour and urinary tract infection.

Given the anti-*Candida* activity of strain CECT 7504, together with its ability to adhere to epithelial cells and to withstand the antimicrobial factors found in the vaginal fluid, in a particular embodiment, the composition of the invention is especially useful in the prevention and/or treatment of vaginal candidiasis. In a more particular embodiment, candidiasis is caused by *Candida glabrata*. As explained above, the strain of the invention is especially useful in the prevention and/or treatment of vaginal candidiasis with a high inflammatory response.

The term "high inflammatory response" in this description is understood as the increase observed during vulvovaginal candidiasis in the concentrations of antimicrobial proteins contained in the vaginal fluid, such as lysozyme, defensins and lactoferrin (Valore, E. V., et al. supra). Lysozyme is one of the antibacterial substances in a higher concentration in vaginal fluid. Its concentration varies between 1 and 4 mg/l in healthy women and women affected by bacterial vaginosis, but can reach 16 mg/l or more in women suffering vulvovaginal candidiasis. Thus, the definition of "high inflammatory response" according to this description can be made based on the levels of lysozyme. It is difficult to establish the levels of lysozyme from which can be considered that there is "a high inflammatory response" because the art does not describe them. In this description it can be considered that "a high inflammatory response" is present when lysozyme concentrations are equal or greater than 4 mg/l.

*Candida* infections can also occur in other epithelia outside of the vaginal tract, such as the intestinal epithelium or the epithelium of the oral cavity. Therefore, the anti-*Candida* activity of strain CECT 7504 and its ability to adhere to epithelium can be useful for the treatment and/or the prevention of *Candida* infections in the intestine or the oral cavity. Thus, in another aspect, the invention provides the composition as defined above for use in the prevention and/or treatment of oral candidiasis and/or intestinal candidiasis. This aspect can be alternatively formulated as the use of a composition as defined in the first aspect of the invention for the manufacture of a pharmaceutical product, a medicament, a food product, an edible product, a food supplement, a medical food, or a personal hygiene product for the prevention and/or treatment of oral and/or intestinal candidiasis. This may be alternatively formulated as a method for the prevention and/or treatment of oral and/or intestinal candidiasis in a human, comprising administering to said human in need thereof an effective amount of the composition as defined in the first aspect of the invention.

Finally, as said above, strain CECT 7504 displays a high capacity to acidify the vaginal medium. Therefore, in another aspect, the invention provides the composition as defined in the first aspect of the invention for use in the prevention and/or treatment of bacterial vaginosis. This aspect can be alternatively formulated as the use of a composition as defined in the first aspect of the invention for the manufacture of a pharmaceutical product, a medicament, a food product, an edible product, a food supplement, a medical food, or a personal hygiene product for the prevention and/or treatment of bacterial vaginosis. This may be alternatively formulated as a method for the prevention and/or treatment of bacterial vaginosis in a human, comprising administering to said human in need thereof an effective amount of the composition as defined in the first aspect of the invention.

The composition of the invention may be prepared in any suitable form which does not negatively affect the viability of the strain forming the composition of the invention. Selection of the excipients and the most appropriate methods for formulation in view of the particular purpose of the composition is within the scope of ordinary persons skilled in pharmaceutical technology. The composition can be administered orally, vaginally or rectally, or using different administration forms simultaneously (e.g. orally and vaginally).

In this sense, the composition of the invention is in solid or liquid form and may be, inter alia, in the form of powders, tablets or lozenges, sucking tablets, film preparations, solutions, aerosols, granules, pills, suspensions, emulsions, capsules, enterocoated tablets and capsules, syrups, liquids, elixirs, sweets, chewing gum, suppositories, micro-enemas, vaginal tablets, vaginal gelatine capsules, creams, gels, ointments, lotions, tampons, napkins, pads, melting strips, condoms, pessaries, sprays, tincture or fluid extracts.

The composition according to the invention can be formulated in a form in which the strain of the invention is the only active agent or is mixed with one or more other active agents and/or is mixed with pharmaceutically acceptable excipients or adequate additives or ingredients in the case of a food product or an edible product. In a particular embodiment of the invention, the composition additionally contains one or more further active agents. Preferably, the additional active agent or agents are other probiotic bacteria which are not antagonistic to the strain forming the composition of the invention. Due to the capacity of the strain of the invention to survive in high concentrations of antimycotic agents typically used to manage *Candida* infections, in a particular embodiment, the composition of the invention can be administered in combination with triazole antimycotic drugs or nistatin in the prevention and/or treatment of candidiasis. Their compatibility has been demonstrated in the examples below. Depending on the formulation, the strain may be added as purified bacteria, as a bacterial culture, as part of a bacterial culture, as a bacterial culture which has been post-treated, and alone or together with suitable carriers or ingredients. Prebiotics could be also added.

The term "pharmaceutical product" is understood in its widely meaning in this description, including any composition that comprises an active ingredient, in this case, the strain of the invention preferably in form of composition, together with pharmaceutically acceptable excipients. The term "pharmaceutical product" is not limited to medicaments. The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts.

The pharmaceutical product can adopt different forms or names depending on the product approval route and also depending on the country. For instance, a medicament is a particular pharmaceutical product. A medical food is another particular pharmaceutical product. The terms "medical food" or "food for special medical purposes" are used in some countries to refer to a food specially formulated and intended for the dietary management of a disease that has distinctive nutritional needs that cannot be met by normal diet alone. They are defined in regulations such as the Food and Drug Administration's 1988 Orphan Drug Act Amendments in the United States, and the Commission Directive 1999/21/EC in Europe. Medical foods are distinct from the broader category of food supplements and from traditional foods that bear a health claim. Thus, in a particular embodiment, the composition of the invention is a medical food.

Often, probiotic bacterial compositions such as the one disclosed herein, are considered as food supplements. A food supplement, also known as dietary supplement or nutritional supplement is considered another particular pharmaceutical product. This is a preparation intended to supplement the diet and provide nutrients or beneficial ingredients that are not usually ingested in the normal diet or may not be consumed in sufficient quantities. Mostly, food supplements are considered as food products, but sometimes they are defined as drugs, natural health products, or nutraceutical products. In the sense of the present invention, food supplements also include nutraceuticals. Food supplements are usually sold "over the counter", i.e. without prescription. If the food supplement adopts the form of a pill or a capsule, it comprises excipients which are the same as the used in medicaments. A food supplement however, can also adopt the form of a food product which is fortified with some nutrients (e.g. a bar or yoghurt).

Thus, in a particular embodiment, the composition of the invention is a food supplement.

If the composition according to the invention is a food supplement, it can be administered as such, can be mixed with a suitable drinkable liquid, such as water, yoghurt, milk or fruit juice, or can be mixed with solid or liquid food. In this context the food supplement can be in the form of tablets or lozenges, pills, capsules, granules, powders, suspensions, sachets, sweets, bars, syrups and corresponding administration forms, usually in the form of a unit dose. Preferably, the food supplement comprising the composition of the invention is administered in the form of tablets, lozenges, capsules or powders, manufactured in conventional processes of preparing dietary supplements.

The strain of the invention can be also included in a variety of food products or edible products, such as a milk products (a yogurt, a cheese, a fermented milk, a milk powder, a milk based fermented product, an ice-cream, a fermented cereal based product, a milk based powder), bread, bars, spreads, biscuits and cereals, a beverage, or a dressing. The term "edible product" is used herein in its broadest meaning, including any type of product, in any form of presentation, which can be ingested by an animal, i.e. a product that is organoleptically acceptable. The term "food product" is understood as an edible product which also provides a nutritional support for the body. Examples of other food products are meat products (e.g. sausages or meat spreads), chocolate spreads, fillings and frostings, chocolate, confectionery, baked goods (cakes, pastries), sauces and soups, fruit juices and coffee whiteners. Particularly interesting food products are food supplements and infant formulas. The food product preferably comprises a carrier material such as oat meal gruel, lactic acid fermented foods, resistant starch, dietary fibres, carbohydrates, proteins and glycosylated proteins. In a particular embodiment the strain of the invention is encapsulated or coated.

Hence, in a particular embodiment, the composition of the invention is a food product or an edible product.

Some of the aforementioned forms are considered medical devices in some countries; e.g. vaginal capsules, a tampon or other types of applicators. Thus, in a particular embodiment, the composition of the invention is a medical device.

In another particular embodiment, the composition of the invention is a personal hygiene product, which can be sold "over the counter" in a supermarket or in a pharmacy. Examples of personal hygiene product are tampons, sanitary napkins, sanitary pads, diapers, soaps, shampoos, gels, ointments, creams, sprays and lotions.

Particularly, the composition of the invention is in the form of disintegrable mucoadhesive intravaginal tablets which are applied intravaginally using an applicator device. The 700 mg tablets particularly comprise hydroxypropylmethylcellulose, anhydrous lactose and citric acid, and 100 mg (1-2×10$^9$ cfu) of strain CECT 7504 (see EXAMPLE 8).

Thus, it has to be understood that the composition of the invention is useful in the management of candidiasis and bacterial vaginosis regardless of the form of the composition; i.e. regardless of being a pharmaceutical product, a medicament, a food product, an edible product, a food supplement, a medical food, or a personal hygiene product.

The strains of the invention are produced by cultivating the bacteria in a suitable medium and under suitable conditions. The strains can be cultivated alone to form a pure culture, or as a mixed culture together with other microorganisms, or by cultivating bacteria of different types separately and then combining them in the desired proportions. After cultivation, the cell suspension is recovered and used as such or treated in the desired manner, for instance, by concentrating or freeze-drying, to be further employed in the preparation of pharmaceutical or edible products. Sometimes the probiotic preparation is subjected to an immobilisation or encapsulation process in order to improve the shelf life. Several techniques for immobilisation or encapsulation of bacteria are known in the art.

It is clear that by using the deposited strain as starting material, the skilled person in the art can routinely, by conventional mutagenesis or re-isolation techniques, obtain further mutants or derivatives thereof that retain or enhance the herein described relevant features and advantages of the strain forming the composition of the invention. In one embodiment of the first aspect of the invention, the mutant is obtained by using recombinant DNA technology. In another embodiment of the first aspect of the invention, the mutant obtained by random mutagenesis. In a third embodiment of the first aspect of the invention, the variant is a naturally occurring variant. Thus, another aspect of the invention relates to a method to obtain a mutant of the strain of *Lactobacillus pentosus* deposited in the Spanish Type Culture Collection under accession number CECT 7504, comprising using the deposited strain as starting material and applying mutagenesis, wherein the obtained mutant retains or enhances the antimycotic and/or antibacterial activities and/or the capacity to colonize the vaginal tract of the parent deposited strain.

The effective amount of colony forming units (cfu) for the strain in the composition will be determined by the skilled in the art and will depend upon the final formulation. For instance, when administered orally, the strain of the invention is present in the composition in an amount giving an effective daily dose of from $10^7$ to $10^{12}$ cfu, according to the current legislation, preferably from $10^9$ to $10^{11}$ cfu and, when administered vaginally or rectally, in an amount giving an effective daily dose of from $10^3$ to $10^{12}$ cfu, preferably from $10^5$ to $10^{19}$ cfu. The term "colony forming unit" ("cfu") is defined as number of bacterial cells as revealed by microbiological counts on agar plates. Food supplements usually contain probiotic strains in an amount ranging from $10^7$ and $10^{12}$ cfu/g. In a particular embodiment, the composition of the invention is a food supplement comprising between $10^9$-$10^{11}$ cfu/g.

The general use of strain CECT 7504 is in the form of viable cells. However, it can also be extended to non-viable cells such as killed cultures or cell lysates (obtained by e.g. exposure to altered pH, sonication, radiation, temperature or pressure, among other means of killing or lysing bacteria) or compositions containing beneficial factors produced by strain CECT 7504.

Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein.

The following examples and drawings are provided herein for illustrative purposes, and without intending to be limiting to the present invention.

EXAMPLES

Figure 1:
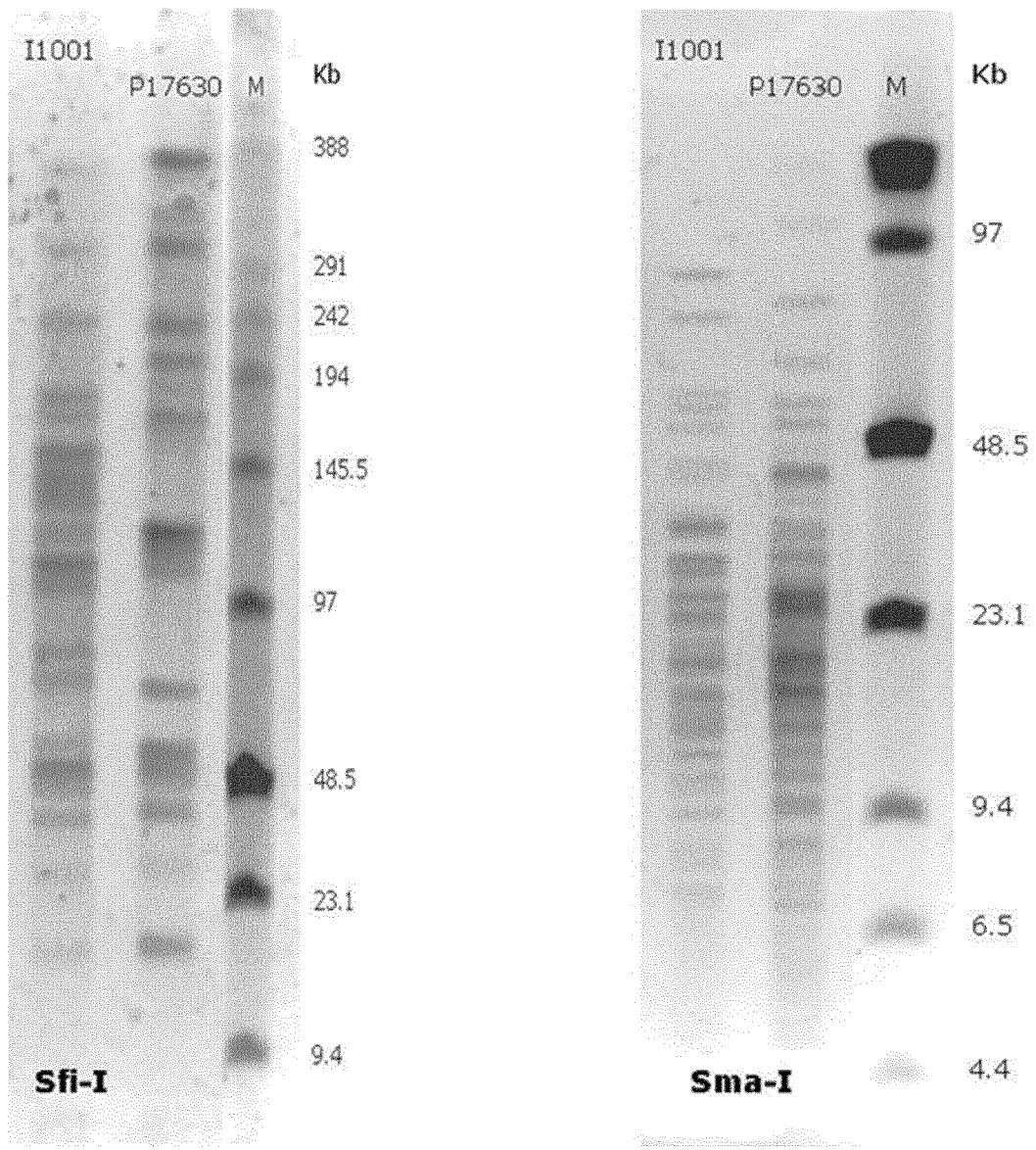
FIG. 1. Pulsed-field electrophoresis patterns of Sma-I and Sfi-I restricted genomic DNA of (from left to right): *Lactobacillus pentosus* CECT 7504 (I1001), *Lactobacillus plantarum* P17630, and DNA molecular marker (M).

As used herein, I1001 corresponds to *Lactobacillus pentosus* CECT 7504.

Example 1. Isolation of the Microorganism

Strain CECT 7504 was isolated from vaginal swabs from healthy young women aged 14-21 years old living under poor hygienic conditions. Samples were dissolved in PBS buffer pH 7.4, aliquoted and plated on different media for incubation under different conditions. Incubation time depended on the growth rate of the strain and run normally from 24 h to 3 days. Isolation of individual strains proceeded with the same selection media, then Gram staining and microscopic examination tests were performed for its initial characterization.

The strain was initially grown in MRS medium supplemented with 100 µg/l novobiocin (Sigma), 5 µg/ml nystatin, 5 µg/ml cyclohexamide (Sigma), 1 mg/l ampicillin and 10 µg/ml vancomycin, and incubated at 30° C. under anaerobic conditions and pH 6.4. Gram staining showed a clear Gram positive staining, as well as non-spore-forming bacilli morphology.

Example 2. Taxonomic Characterization of Strain

Bacteria were harvested, washed and resuspended in pre-lysis buffer (480 ml EDTA 50 mM, pH 8.0; 120 ml lysozyme 10 mg/ml) at 37° C. for 60 min. DNA was extracted using Wizard genomic DNA purification kit (Promega). After centrifugation of the pre-treated bacteria at 14000 g for 2 min to remove the supernatant, the Promega's protocol was followed. In brief, bacteria were resuspended in Nuclei Lysis Solution and incubated at 80° C. for 5 min, then cooled to room temperature. Cell lysates were incubated in RNase solution at 37° C. for 60 min and proteins were precipitated by adding the Protein Precipitation Solution and vortexing at high speed. Samples were cooled down and centrifuged at 15000 g for 3 min. The supernatants containing the DNA were transferred to clean 1.5 ml microfuge tubes and mixed with 600 ml of isopropanol by inversion. DNA was collected by centrifugation at 15000 g for 2 min and carefully pouring off the supernatant. DNA samples were washed with 600 ml of 70% ethanol by gently inverting the tube several times. Ethanol was removed by aspiration, after centrifugation at 15000 g for 2 min. Finally, the DNA pellet was resuspended in 100 ml of Rehydration Solution by incubating at 65° C. for 1 h. Samples were stored at 2-8° C.

2.1. Genus and Species Identification

The 16S rRNA was amplified by PCR using the universal primers Eub27f and Eub1492r, which produce a fragment nearly full-sequence of the 16S gene (more than 1,400 nucleotides) (TABLE 1). Then, the DNA was washed using the kit Qiaquick (Qiagen).

*Lactobacillus pentosus* or *Lactobacillus plantarum*. It is known that *Lactobacillus plantarum, paraplantarum* and *pentosus* species are closely related, thus being interchangeable in practice.

2.2. Strain Genotyping

Characterization was performed by genomic digestion and pulsed-field gel electrophoresis (PFGE). CECT 7504 strain was subjected to a previously described protocol (Rodas, A. M., et al. Polyphasic study of wine *Lactobacillus* strains: taxonomic implications. *Int J Syst Evol Microbiol.* 2005, Vol. 55, No. 1, pages 197-207) with minor modifications. Strains were grown on MRS agar plates and incubated at 37° C., 5% $CO_2$ for 18 h. Cells were harvested and washed 3 times in 8 ml PET (10 mM Tris pH 7.6, 1 M NaCl) then centrifuged at 6000 rpm 10 min. Pellets were resuspended in 700 ml lysis buffer (6 mM Tris, 1 M NaCl, 0.1 M EDTA, 0.5% SLS, 0.2% deoxycholic acid; 1 mg/ml lysozyme; 40 U/ml mutanolysin; 20 mg/ml RNase). An equal volume of 1.6% low melting point agarose (FMC BioProducts, Rockland, Me., USA) was added to the resuspended cells and solidification was allowed at 4° C. for 1 h. Inserts were transferred to 2 ml lysis buffer II (0.5 M EDTA pH 9.2, 1% N-lauryl sarcosine and 1 mg/ml pronase) and incubated at

TABLE 1

Primers used for amplifying and sequencing the 16S gene

| Step | Primer | Orientation | 5' → 3' Sequence |
|---|---|---|---|
| Amplification | Eub27f | forward | GAGTTTGATCCTGGCTCAG (SEQ ID NO: 1) |
|  | Eub1492r | reverse | TACGGYTACCTTGTTACGACTT (SEQ ID NO: 2) |
| Sequencing | 27f | forward | AGAGTTTGATCCTGGCTCAG (SEQ ID NO: 3) |
|  | 357f | forward | CGCCCGCCGCGCCCCGCGCCCGGCCCGCCGCC CCCGCCCCCCTACGGGAGGCAGCAG (SEQ ID NO: 4) |
|  | 907r | reverse | CCGTCAATTCCTTTGAGTTT (SEQ ID NO: 5) |
|  | 1492r | reverse | GGTTACCTTGTTACGACTT (SEQ ID NO: 6) |

Four consecutive sequencing reactions were performed for each sample in a Genetic Analyzer 3130 (Applied Biosystems) using BigDye kit v. 3.1 and the primers shown in TABLE 1. Data collection and chromatograms were built using DNA Sequence Analysis v. 5.2 software (Applied Biosystems) and checked by visual analysis with Chromas (Technelysium Pty Ltd.) and BioEdit (Ibis Biosciences). SEQ ID NO: 7 is the sequence of the 16S gene of strain CECT 7504.

Genus Identification was carried out using the Ribosomal Database Project (RDP) tools (Wang Q., et al. Naive Bayesian Classifier for Rapid Assignment of rRNA Sequences into the New Bacterial Taxonomy. *Appl. Environ. Microbiol.* 2007, Vol. 73, No. 16, pages 5261-5267). Species identification was performed by comparison of the sequence obtained with 16S sequences of type strains, in the Ribosomal Database Project (Cole, J. R., et al. The Ribosomal Database Project (RDP-II): introducing myRDP space and quality controlled public data. *Nucl. Acids Res.* 2007, Vol. 35(suppl_1), pages D169-172). Closest match was *Lactobacillus pentosus* strain JCM 1558 (100% maximum similarity score) which is the type strain of the species *Lactobacillus pentosus*. 16S sequence of the strain CECT 7504 was also aligned to NCBI sequence database using BLAST resulting in a closest match with *Lactobacillus plantarum* strain KLDS1.0676. Due to the fact that the sequence databases are dynamic by continuously incorporating new genetic sequences, the strain CECT 7504 can be classified as 50° C. for 48 h. Then inserts were washed at room temperature with TE buffer (10 mM Tris, 1 mM EDTA pH 8.0). Total DNA digestion was performed separately by Sfi-I and Sma-I restriction enzymes (Roche Diagnostics). Commercial probiotic strain *L. plantarum* P17630 was used as control.

Pulsed-field gel electrophoresis was carried out using CHEF DRIII apparatus (BioRad Laboratories). Inserts were loaded in a 1% agarose gel (SeaKem ME agarose, FMC BioProducts, ME, USA). TABLE 2 describes electrophoresis conditions for each enzyme. DNA MW markers were Lambda ladder PFG Marker and Low Range PFG Marker (New England Biolabs). After electrophoresis, gels were stained with ethidium bromide and UV using GelDoc System (BioRad). The results are depicted in FIG. 1.

TABLE 2

Electrophoresis conditions for this study.

| Enzyme | Block | Initial Pulse (sec) | Final pulse (sec) | Time (hours) |
|---|---|---|---|---|
| Sfi-I | 1 | 2 | 10 | 10 |
|  | 2 | 15 | 25 | 6 |
| Sma-I | 1 | 0.5 | 5 | 16 |

As shown in FIG. 1, pulsed-field gel electrophoresis Sfi-I and Sma-I restriction patterns were different for the strain of the invention *L. pentosus* CECT 7504 (I1001) and a commercial control strain belonging to the closely related species *L. plantarum* (P17630). PFGE allows distinguishing between strains of the same species, and thus can be used to uniquely identify a given bacterial strain within a bacterial species (Rodas, A. M., et al. 2005 supra).

Example 3. Resistance to the Vaginal Fluid

The vaginal fluid contains a large variety of antimicrobial factors which act by different mechanisms, such as acidic pH, lysozyme, lactoferrin and defensins. Therefore, demonstrating that a bacterial strain is able to survive in an acidic environment (Dho, G., et al. Microbial characteristics of *Lactobacillus plantarum* P17630 contained in vaginal suppositories. *GIMMOC*. 2003. Vol. VII, No. 2, pages 102-8) is not sufficient guarantee that this strain will be able to survive in vaginal environment, because it contains other antimicrobial factors in addition to acidic pH.

Vaginal Fluid (Synthetic)

A vaginal fluid simulant was used (Owen, D. H. et al. A vaginal fluid simulant. *Contraception*. 1999, Vol. 59, No. 2, pages 91-5), to which antibacterial proteins and peptides were added: 3.5 g/l NaCl, 1.4 g/l KOH, 0.22 g/l $Ca(OH)_2$, 0.02 g/l BSA, 2 g/l lactic acid, 1 g/l acetic acid, 0.16 g/l glycerol, 0.4 g/l urea and 5 g/l glucose. pH was further adjusted to 4.2 using lactic acid.

Antibacterial Proteins

Lysozyme is one of the antibacterial substances in a higher concentration in vaginal fluid. Its concentration varies between 1 and 4 mg/l in healthy women and women affected by bacterial vaginosis, but can reach 16 mg/l or more in women suffering vulvovaginal candidiasis (Valore, E. V., et al. 2006, supra). Lysozyme has broad spectrum antibacterial activity, but is especially active against bacteria such as *Lactobacilli*. Therefore it is of great importance to ensure the selection of a strain able to survive to high concentrations of lysozyme in order to obtain a probiotic that can benefit all women with vulvovaginal candidiasis.

Antibacterial Peptides

The activity of defensins β-2 and β-3 against *Lactobacillus* has been well documented. However, defensin β-2 is found in a concentration 30 times lower than defensin β-3 (Ghosh, S. K., et al. Quantification of Human beta-defensin-2 and -3 in Body Fluids: Application for Studies of Innate Immunity. *Clin Chem*. 2007, Vol. 53, No. 4, pages 757-765). Concentration of defensin β-3 in vaginal fluid may lie between 1 and 5 mg/l.

Conversely, other antimicrobial proteins such as lactoferrin have little activity against *Lactobacillus*, e.g. antibacterial activity of lactoferrin is mainly based on disruption of the metabolism of bacterial iron and *Lactobacilli* do not require iron to grow (Archibald, F., Manganese: its acquisition by and function in the lactic acid bacteria. *Crit Rev Microbiol*. 1986, Vol. 13, No. 1, pages 63-109).

*Lactobacilli* strains were grown overnight in MRS broth. Cells were harvested by centrifugation and resuspended in PBS at $10^7$ cfu/ml. 20 μl of the cell suspension were inoculated in 200 μl of vaginal fluid simulant supplemented with lysozyme (0, 4 and 16 mg/l final concentration) or 4 mg/l lysozyme plus 13-3 defensin (0, 2 and 4 mg/l final concentration). Microtiter plates were incubated for 3 h at 37° C. and the number of viable cells remaining in each well was counted by serial dilution and plating in MRS agar. All experiments were performed in triplicate.

Figure 2:
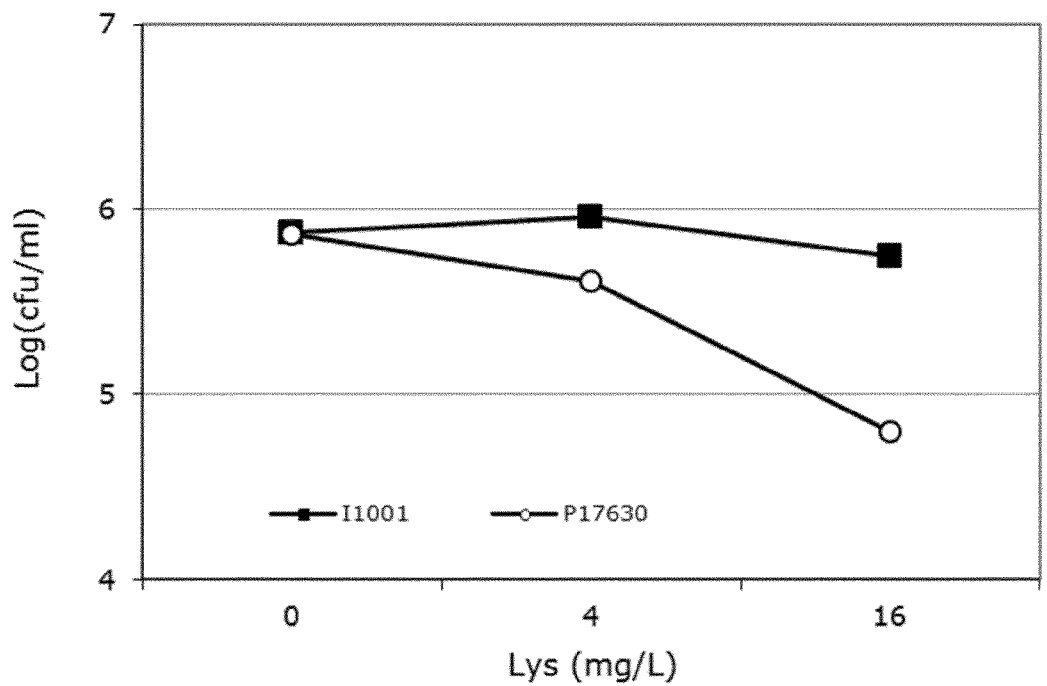
FIG. 2 shows the growth of *Lactobacilli* strains in vaginal fluid simulant supplemented with lysozyme (0, 4 and 16 mg/l final concentration). "Lys" means "Lysozyme". I1001 is the strain CECT 7504 and P17630 is the control strain *L. plantarum* P17630.
Figure 3:
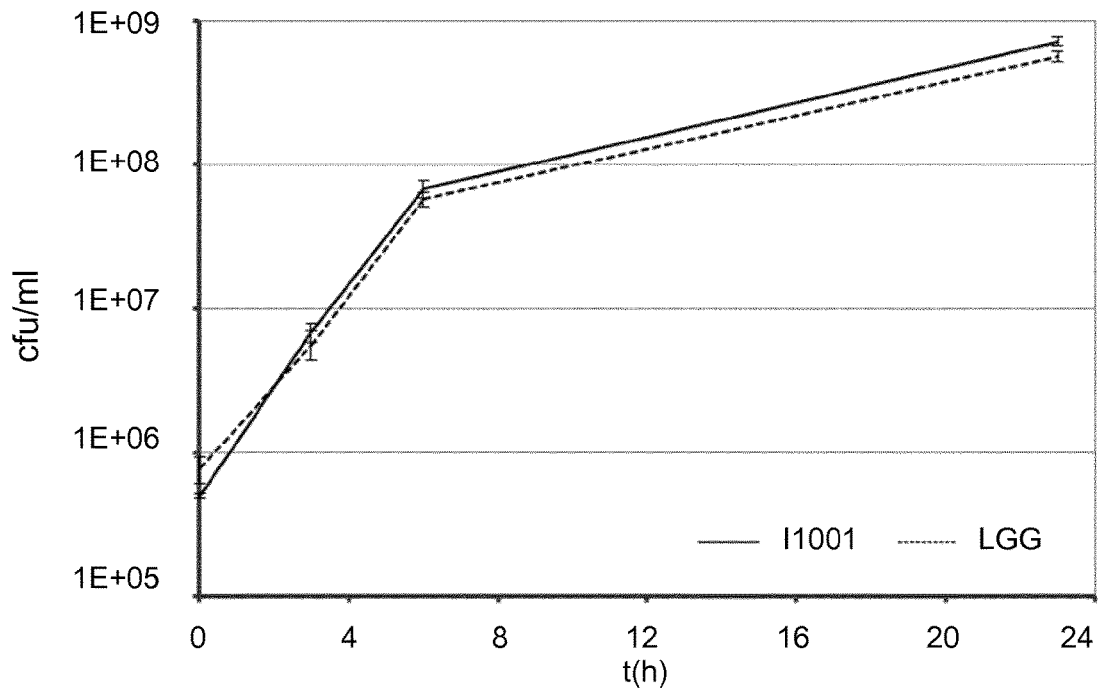
FIG. 3 shows how strain *L. pentosus* CECT 7504 (I1001) displays a growth comparable to that of the well-known probiotic *L. rhamnosus* GG in culture medium simulating industrial media; "t" stands for "time" and cfu/ml is the number of viable cells.

Of 10 isolated *Lactobacilli* strains, strain CECT 7504 was among the five strains showing resistance both to lysozyme and β-3 defensin. Strain CECT 7504 showed a high resistance to lysozyme concentrations up to 16 mg/l (see FIG. 2). On the other hand, the control strain *L. plantarum* P17630 (ISADIN) showed a marked decrease in viability (90%) when exposed concentrations of lysozyme above 4 mg/l, such as the ones that can be found in a significant fraction of vulvovaginal candidiasis patients.

Of note, both strain CECT 7504 and strain *L. plantarum* P17630 were resistant to concentrations of β-3 defensin of 2 mg/l and 4 mg/l, either alone or combined with 4 mg/l of lysozyme, indicating that both are prepared to survive in the environment of a healthy vagina.

Example 4. Anti-Microbial Properties 4.1. Activity Against *C. albicans* and *C. glabrata*

Activity against *C. albicans* and *C. glabrata* was tested using the agar overlay method. Briefly, *Lactobacilli* strains were grown overnight in MRS agar (Scharlab) and plated with a sterile bacteria loop as two crossing straight lines. Plates were incubated for 24 h at 37° C. and subsequently overlayed with 6 ml of melted YM medium (Scharlab) inoculated with 20 μl of an overnight culture of *Candida* in YM broth. Plates were allowed to cool and were incubated again for 14 h and the zone of inhibition was measured at three different points. *Lactobacilli* strains were initially tested against one strain of *C. albicans* (CECT 1392). Strains displaying significant activity were subsequently tested against four more strains of *Candida*: *C. albicans* CECT 1472 and CECT 1002 and *C. glabrata* CECT 1448 and CECT 1900. All experiments were performed in triplicate.

Of 46 *Lactobacilli* strains isolated from vaginal samples, 35 showed significant activity against *C. albicans* CECT 1392. However, only 8 *Lactobacilli* strains displayed significant activity against all three strains of *C. albicans*. Moreover, only 3 *Lactobacilli* strains displayed significant activity both against *C. albicans* and *C. glabrata* strains. A sample of the results is shown in TABLE 3.

TABLE 3

| Probiotic strain | *C. albicans* CECT 1392 | *C. albicans* CECT 1472 | *C. albicans* CECT 1002 | *C. glabrata* CECT 1448 | *C. glabrata* CECT 1900 |
|---|---|---|---|---|---|
| CECT 7504 | ++ | + | +++ | ++ | + |
| P17630 | + | + | ++ | + | − |
| Isolate 1036 | + | + | − | − | − |
| Isolate 1048 | + | + | − | − | − |
| Isolate 1056 | + | + | − | − | − |
| Isolate 2029 | + | + | ++++ | ++ | + |
| Isolate 2058 | + | + | ++ | − | − |
| Isolate 2099 | + | + | − | − | − |

TABLE 3-continued

| Probiotic strain | C. albicans CECT 1392 | C. albicans CECT 1472 | C. albicans CECT 1002 | C. glabrata CECT 1448 | C. glabrata CECT 1900 |
|---|---|---|---|---|---|
| Isolate 3103 | + | + | − | − | − |
| Isolate 3124 | + | + | − | − | − |
| Isolate 3172 | + | + | ++ | + | − |

Degree of inhibition:
+++ >5 mm;
++ 3-5 mm;
+ 1-3 mm;
− no inhibition

Strain CECT 7504 showed higher activity against the three strains of C. albicans when compared to the commercial probiotic strain Lactobacillus plantarum P17630. Most wild-type Lactobacilli tested showed activity against two strains at most. Also, strain CECT 7504 showed high activity against one strain of C. glabrata and some activity against a second strain, while both L. plantarum P17630 and other wild-type strains showed low activity against the first strain and no activity against the second strain (TABLE 3).

4.2. Acidification of the Vaginal Environment

It is widely accepted that one of the fundamental functions of the healthy vaginal flora is the acidification of the vaginal fluid to prevent overgrowth of undesirable bacterial species, i.e. bacterial vaginosis, mostly through the production of lactic and acetic acids. Thus, high production of lactic acid is a desirable trait for a probiotic strain for the management of bacterial vaginosis.

The ability to acidify the vaginal fluid is often extrapolated from the ability of the strains to acidify typical laboratory culture media or milk. However, the composition of the vaginal fluid (low concentration of nutrients) is quite different from the composition of typical laboratory culture media or milk, which are nutrient-rich. Therefore assuming that a strain has a good capacity to survive, grow and acidify the vaginal fluid because of its ability to survive, grow and acidify a medium with a different composition is at least risky.

In order to detect the potential to acidify the vaginal fluid, a modified vaginal fluid simulant was used (Owen, D. H. et al. 1999, supra) supplemented with 4 mg/l of lysozyme (the highest concentration observed in bacterial vaginosis (Valore, E. V., et al. 2006, supra): 3.5 g/l NaCl, 1.4 g/l KOH, 0.22 g/l Ca(OH)$_2$, 0.02 g/l BSA, 2 g/l lactic acid, 1 g/l acetic acid, 0.16 g/l glycerol and 0.4 g/l urea. pH was adjusted to 5.5 using NaOH 1N and glucose was added at 20 g/l to be able to detect a drop in pH caused by fermentation.

Lactobacilli strains were grown overnight in MRS broth and 50 μL were inoculated in 3 ml of modified vaginal fluid simulant. pH was measured after overnight incubation at 37° C. All experiments were performed in triplicate.

Strain CECT 7504 displayed the highest capacity to acidify the vaginal fluid among the Lactobacilli strains tested, which was significantly higher than the capacity displayed by control strain P17630 (TABLE 4). The acidification capacity of strain CECT 7504 was also the best among the isolates with the highest activity against Candida.

TABLE 4

| Probiotic strain | Final pH (average ± S.E.M.) | Statistical difference vs. control (1-way ANOVA with Dunnett's post-hoc test) |
|---|---|---|
| CECT 7504 | 4.44 ± 0.05 | P < 0.05 (better than control) |
| Isolate 2029 | 4.55 ± 0.03 | P > 0.05 |
| Isolate 2058 | 4.69 ± 0.04 | P > 0.05 |
| Isolate 3096 | 4.70 ± 0.01 | P > 0.05 |
| Isolate 3146 | 4.56 ± 0.01 | P > 0.05 |
| Isolate 3172 | 4.70 ± 0.02 | P > 0.05 |
| P17630 (control) | 4.59 ± 0.02 | — |

Example 5. Adhesion to Cells of the Vaginal Epithelium

Lactobacilli strains labelled with tritiated thymidine were incubated with confluent cultures of HeLa cells, a cell line obtained from the epithelium of the vaginal cervix previously used to evaluate the adherence of Lactobacilli to the vaginal epithelium (Atassi, F., et al. Lactobacillus strains isolated from the vaginal microbiota of healthy women inhibit Prevotella bivia and Gardnerella vaginalis in coculture and cell culture. FEMS Immunology & Medical Microbiology. 2006, Vol. 48, No. 3, pages 424-432; Mastromarino, P., et al. Characterization and selection of vaginal Lactobacillus strains for the preparation of vaginal tablets. Journal of Applied Microbiology. 2002, Vol. 93, No. 5, pages 884-893). This methodology allows counting all adhered Lactobacilli cells instead of taking partial samples of epithelial cells and performing visual counts of adhered Lactobacilli by microscopy, resulting in more reliable counts.

Our experience shows us that the preincubation in acid medium (such as the vaginal fluid) could alter the adherence of bacteria, mainly due to expression of HSP proteins in the membrane. Moreover, it is important to note that the present studies have been performed on a confluent monolayer of epithelial cells to simulate the real conditions of the epithelium, not on individual epithelial cells in solution as reported for other probiotics (Culici, M., et al. Adhesion of Lactobacillus plantarum P17630 to vaginal epithelial cells and its influence on Candida albicans adhesion. GIMMOC. 2004, Vol. 8, No. 1, pages 34-41).

HeLa cells were grown to 95-100% confluence in 24-well plates. Lactobacilli strains were cultured overnight in 10 ml of MRS medium with tritiated thymidine (10 μCi). Then, bacterial cells were harvested by centrifugation and resuspended at $5 \times 10^8$ cfu/ml in vaginal fluid simulant with pH adjusted to 5 using lactic acid for 15 min at 37° C. 0.5 ml aliquots were diluted in PBS to obtain suspensions of $2 \times 10^7$ cfu/ml and $2.5 \times 10^6$ cfu/ml, which are roughly equivalent to bacterial to HeLa cell ratio of 200:1 and 25:1, respectively.

Half ml of the bacterial suspensions were added to the wells containing confluent cultures of HeLa cells and co-incubated for 45 min at 37° C. Then, wells were washed twice with PBS to remove bacteria loosely adherent. Finally, wells were scrapped and the content was placed in scintillation vials to quantify the amount of tritiated thymidine. Also, aliquots of the bacterial suspensions inoculated in the 24-well plates were placed in scintillation vials to calculate the ratio between radioactivity and bacterial cells for each strain. All experiments were performed in duplicate.

Strain CECT 7504 displayed higher adherence to vaginal epithelial cells than control strain P17630 as it is shown in the table below (TABLE 5):

TABLE 5

| Probiotic strain | Bacteria to cell ratio 200:1 | Bacteria to cell ratio 25:1 |
|---|---|---|
| CECT 7504 | $2.35 \pm 0.85 \times 10^5$ bacteria/well | $1.70 \pm 0.30 \times 10^4$ bacteria/well |
| P17630 | $1.05 \pm 0.55 \times 10^5$ bacteria/well | $0.95 \pm 0.05 \times 10^4$ bacteria/well |

Example 6. Growth in Industrial Medium

A 0.5% inoculum of an overnight culture of each strain to be tested was inoculated in 100 ml of General Edible Medium (Saarela, M., et al. Stationary-phase acid and heat treatments for improvement of the viability of probiotic lactobacilli and bifidobacteria. *Journal of Applied Microbiology.* 2004, Vol. 96, No. 6, pages 1205-1214) pre-heated at 37° C., which was used as a surrogate of industrial media. This medium is composed by 20 g/l glucose, 30 g/l soy peptone, 7 g/l yeast extract, 1 g/l $MgSO_4 \times 7\ H_2O$ in K-phosphate buffer 0.01 M (pH 6.3). Strains were incubated at 37° C. and 100 μL aliquots were extracted at different time points (0, 3, 6 and 23 hours) in order to quantify the number of viable cells by plate counting. Strain *Lactobacillus rhamnosus* GG (Valio Ltd), a well-known probiotic, was used as a control.

Strain *L. pentosus* CECT 7504 (I1001) displays a growth comparable to that of the well-known probiotic *L. rhamnosus* GG in medium simulating industrial media, reaching concentrations of $10^9$ cfu/ml after an overnight culture starting from an inoculum of $10^6$ cfu/ml.

Example 7. Vaginal Tolerance in Rabbits after Repeated Administration

The tolerability in the vaginal mucosa was determined after administration of strain CECT 7504 at two different concentrations (20 and 100 mg/ml, at $5 \times 10^7$ cfu/mg) compared to a control group (vehicle only), following the ISO 10993-10:2002 guideline. New Zealand White female rabbits of 9-11 weeks of age, weighting 2.1-2.5 kg, were randomized in three groups of 6 rabbits each and maintained in individual cages at 17-20° C. and 50-70% relative humidity, and fed standard Teklad 2030C rabbit diet and tap water ad libitum. Each rabbit was administered at the dose of 1 ml/day once a day for 7 consecutive days by topical route to rabbit vagina. 1% Sodium Carboxymethyl Cellulose in distilled water was used as vehicle. The pH of the formulations was 7.6 for vehicle alone, 5.8 for the 20 mg/ml dose and 5.6 for the 100 mg/ml dose.

Mortality was checked twice daily and clinical signs once daily. Body weight was checked twice during acclimatization, immediately before the first and fourth administration, and prior to sacrifice. All animals were sacrificed 24 hours after the last administration by intravenous injection of sodium pentobarbital administered into the ear vein at a dose of 60 mg/kg body weight and a volume of 1 ml/kg, and necropsied. The genital apparatus of each animal was examined with special emphasis on the vaginal surface.

After separating the fat and the adjacent tissues, the ovaries, the vagina and the uterus of each animal were fixed in 10% neutral buffered formalin. Sections of the distal, medial and proximal zones of the vagina were embedded, cut at a thickness of 4 micrometers, and stained with hematoxylin and eosin, and were microscopically examined, grading the alterations observed according to the following evaluation scale (TABLE 6):

TABLE 6

| Reaction Grading | | Numerical rating |
|---|---|---|
| 1. Epithelium | Normal, intact | 0 |
| | Cell degeneration or flattening | 1 |
| | Metaplasia | 2 |
| | Focal erosion | 3 |
| | Generalized erosion | 4 |
| 2. Leukocyte infiltration (per 400x power field) | Absent | 0 |
| | Minimal (<25) | 1 |
| | Mild (26-50) | 2 |
| | Moderate (51-100) | 3 |
| | Marked (>100) | 4 |
| 3. Vascular congestion | Absent | 0 |
| | Minimal | 1 |
| | Mild | 2 |
| | Moderate | 3 |
| | Marked, with disruption of vessels | 4 |
| 4. Edema | Absent | 0 |
| | Minimal | 1 |
| | Mild | 2 |
| | Moderate | 3 |
| | Marked | 4 |

The evaluation of the tolerability and irritant properties of the test item is done based on the mean scores obtained. The microscopic evaluation grades for all animals in the test group are added and the sum is divided by the number of observations to obtain a test group average, mean value of irritation (MVI). The maximum score is 16. It is repeated for the Control group. The Control group average is subtracted from the test group average to obtain the Irritation Index, and it is classified according to the following scale (TABLE 7):

TABLE 7

| Average Grade | Irritation Index (MVI) |
|---|---|
| 0 | None |
| 1 to 4 | Minimal |
| 5 to 8 | Mild |
| 9 to 11 | Moderate |
| 12 to 16 | Severe |

Clinical Signs

Neither mortality nor clinical signs of systemic toxicity were observed during the study period, and all animals survived to scheduled necropsy. No noticeable differences in body weight or body-weight gain were observed in Group 2 (20 mg/ml dose). Body-weight loss was recorded in two females from Group 3 (100 mg/ml dose). However, differences were not statistically significant (Dunnett-Test) with respect to the Control group.

Macroscopic and Microscopic Findings

An increased incidence of reddish discoloration of the vaginal mucosa compared to the Control group was observed after 7 days of topical administration of strain CECT 7504 at the concentrations of 20 mg/ml and 100 mg/ml ($5 \times 10^7$ cfu/mg). Inflammation in the vaginal submucosa as well as increased incidence and/or severity of vascular congestion and leukocyte infiltration due to an immune response was observed. However, the response was dose-dependent, and the alterations were of minimal severity at 20 mg/kg and slight at 100 mg/kg. Overall, the mean irritation value (MIV) obtained in Group 2 was 0.83 indicating no irritative response at the concentration of 20 mg/ml. The mean irritation value (MIV) obtained in Group 3 was 2.33 indicating minimal irritation at the concentration of 100 mg/ml. It must be considered that the genital tract mucosal microflora in rabbit is very scarce, containing basically *Staphylococcus, Micrococcus* and *Pseudomonas* (Jacques, M., et al. The normal microflora of the female rabbit's genital tract. *Can J Vet Res*. 1986, Vol. 50, pages 272-4). So, unlike human vaginal flora, there are almost no *lactobacilli* and, therefore, an immune reaction to foreign body was observed after the administration of *Lactobacillus pentosus* CECT 7504.

Example 8. Vaginal Colonization and Tolerability in Female Volunteers after Repeated Administration An open-label clinical trial was conducted in 10 healthy female volunteers aged 18-40 years, in order to determine the ability of strain CECT 7504 to colonize the vaginal epithelium (as primary endpoint) and to assess the tolerability of the product (as secondary endpoint). Administration was tested for 3 and 5 days to assess if the duration of the exposure to the probiotic influenced its ability to colonize the vaginal epithelium. Inclusion criteria were having regular menses and willingness to abstain from sexual activity during the days of product administration and on the night before sampling days. Women using intravaginal products, having vaginal infection or taking antibiotics from 15 days before the onset of the study were excluded, as well as immunosuppressed, lactating or pregnant women. The protocol was reviewed and approved by the ethics committee of Hospital Vail d'Hebron (Barcelona) and was conducted in accordance to the Helsinki Declaration and Good Clinical Practice guidelines.

Disintegrable mucoadhesive intravaginal tablets of 700 mg made of hydroxypropylmethylcellulose (HPMC), anhydrous lactose and citric acid, and containing 100 mg ($1-2 \times 10^9$ cfu) of strain CECT 7504 were prepared, with a compression force of 60 N. Volunteers (21-36 years old, median 29 years old) were randomized to receive tablets either for 3 consecutive days (5 women) or 5 consecutive days (5 women). Tablets were applied intravaginally by the volunteers before going to sleep, using an applicator device. Sterile swabs were used to collect samples of vaginal fluid right before the first administration and on days 1, 3 and 8 after the last administration. Samples were stored at 4° C. until analysed. To assess tolerability, volunteers recorded vaginal symptoms daily for 3 weeks from the first day of administration of the vaginal tablets.

DNA was extracted from the samples using EasyMag automated system (Biomerieux) and samples were tested for the presence of CECT 7504 strain using a quantitative PCR specific for the *L. pentosus* and *L. plantarum* and species. Amplification was targeted to a region of 144 base pairs within the 16S-23S rRNA intergenic region. The probe was 5'-labelled with FAM and 3'-labelled with NFQ-MGB (Applied Biosystems). Amplification was conducted by using the TaqMan Universal Master Mix (Applied Biosystems) following manufacturer's instructions. Warm-up consisted of 2 minutes at 50° C. and 10 minutes at 95° C.

Denaturation was performed at 95° C. for 15 sec followed by annealing and extension at 60° C. for 60 sec, for 45 cycles. The sequences of the primers and the probe are indicated below (TABLE 8).

TABLE 8

| | 5' → 3' Sequence |
|---|---|
| Forward primer | TGGATCACCTCCTTTCTAAGGAAT (SEQ ID NO: 8) |
| Reverse primer | TGTTCTCGGTTTCATTATGAAAAAATA (SEQ ID NO: 9) |
| Probe | ACATTCTTCGAAACTTTGT (SEQ ID NO: 10) |

Figure 4:
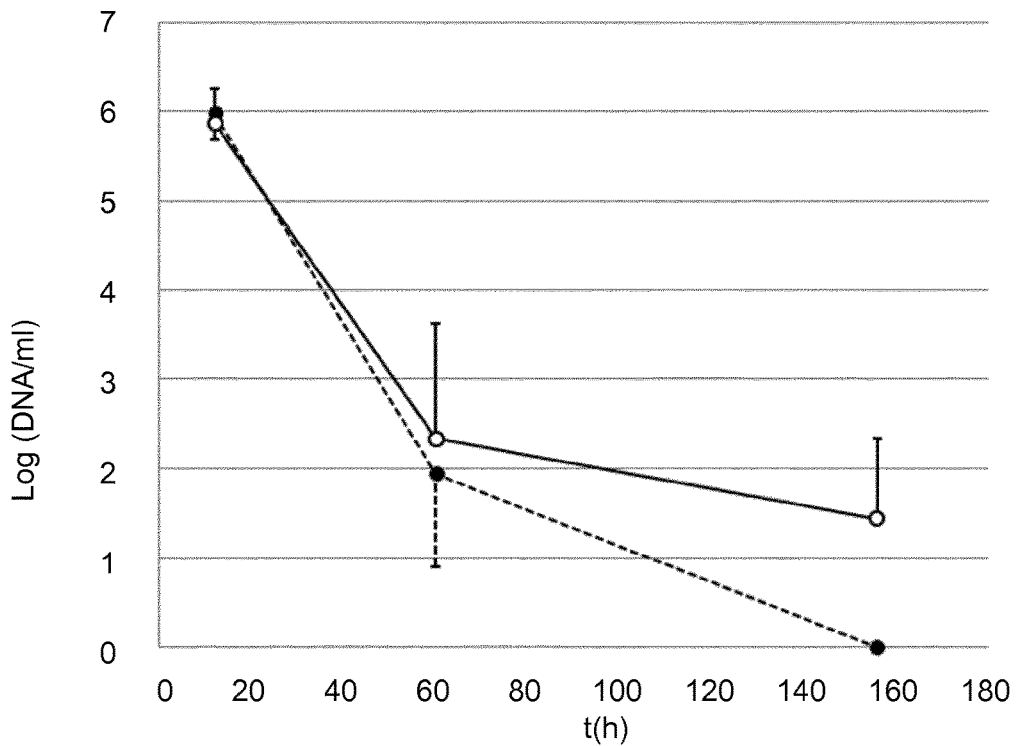
FIG. 4 shows the amount of DNA of the species *L. pentosus* and *L. plantarum* found in the vaginal fluid of the female volunteers participating in the study after the last administration of the product. Data depicts average and SEM values. Time is indicated in hours after the last administration; DNA copies per ml of vaginal fluid are on a logarithmic scale. Open circles correspond to data from volunteers taking the product for 5 consecutive days, and closed circles corresponds to data from volunteers taking the product for 3 consecutive days.

The probiotic was found to be well tolerated. Mild vaginal discharge was reported by some volunteers, but in other studies it has been shown to be attributable to the introduction of the product into the vagina and not to the probiotic strain, as this effect is also observed in volunteers receiving placebo product (Stapleton A. E, et al. Randomized, Placebo-Controlled Phase 2 Trial of a *Lactobacillus* crispatus Probiotic Given Intravaginally for Prevention of Recurrent Urinary Tract Infection. *Clinical Infectious Diseases*. 2011, Vol. 52, Vol. 10, pages 1212-17). No detectable DNA of *L. pentosus* or *L. plantarum* strains was found at baseline in the volunteers. However, $10^6$ DNA copies per ml of vaginal fluid were found on average in the morning after the last administration of the probiotic (FIG. 4). Two days later, the probiotic was still detectable regardless of the group. In 2 out of 5 patients in the group that received the tablet for 5 consecutive days the probiotic was still detectable 8 days after the last administration, but not in those receiving the product for 3 days.

BIBLIOGRAPHIC REFERENCES

Araya, M., et al. Guidelines for the Evaluation of Probiotics in Food—Joint FAO/WHO Working Group, FAO/WHO. Editor 2002. Food and Agriculture Organization of the United Nations and World Health Organization: Ontario, Canada.

Anukam, K. C., et al. Clinical study comparing probiotic *Lactobacillus* GR-1 and RC-14 with metronidazole vaginal gel to treat symptomatic bacterial vaginosis. *Microbes and Infection*. 2006, Vol. 8, Nos. 12-13, pages 2772-2776.

Larsson, P. G., et al. Human lactobacilli as supplementation of clindamycin to patients with bacterial vaginosis reduce the recurrence rate; a 6-month, double-blind, randomized, placebo-controlled study. *BMC Women's Health*. 2008, Vol. 8, No. 1, page 3.

Richter, S. S., et al. Antifungal Susceptibilities of *Candida* Species Causing Vulvovaginitis and Epidemiology of Recurrent Cases. *J. Clin. Microbiol*. 2005, Vol. 43, No. 5, pages 2155-2162.

Valore, E. V., et al. Reversible Deficiency of Antimicrobial Polypeptides in Bacterial Vaginosis. *Infect. Immun*. 2006, Vol. 74, No. 10, pages 5693-5702.

Martinez, R. C. R., et al. Improved treatment of vulvovaginal candidiasis with fluconazole plus probiotic *Lactobacillus rhamnosus* GR-1 and *Lactobacillus reuteri* RC-14. *Letters in Applied Microbiology*. 2009, Vol. 48, No. 3, pages 269-274.

Okkers, D. J. et al. Characterization of pentocin TV35b, a bacteriocin-like peptide isolated from *Lactobacillus pentosus* with a fungistatic effect on *Candida albicans*. *Journal of Applied Microbiology*. 1999, Vol. 87, No. 5, pages 726-734.

Dimitonova, S. P. et al. Antimicrobial activity and protective properties of vaginal *lactobacilli* from healthy Bulgarian women. *Anaerobe*. 2007, Vol. 13, No. 5-6, pages 178-184.

Pascual, L. M. et al. *Lactobacillus rhamnosus* L60, a potential probiotic isolated from the human vagina. *Journal of General and Applied Microbiology*. 2008, Vol. 54, No. 3, pages 141-148.

Andreoletti, O., et al. The maintenance of the list of QPS microorganisms intentionally added to food or feed. Question no: EFSA-Q-2008-006. *The EFSA Journal*. 2008, Vol. 923, pages 1-48.

Bories, G., et al. Update on the criteria used in the assessment of bacterial resistance to antibiotics of human or veterinary importance. *The EFSA Journal*. 2008, Vol. 732, pages 1-15.

Wang, Q., et al. Naive Bayesian Classifier for Rapid Assignment of rRNA Sequences into the New Bacterial Taxonomy. *Appl. Environ. Microbiol.* 2007, Vol. 73, No. 16, pages 5261-5267.

Cole, J. R., et al. The Ribosomal Database Project (RDP-II): introducing myRDP space and quality controlled public data. *Nucl. Acids Res.* 2007, Vol. 35(suppl_1), pages D169-172.

Rodas, A. M., et al. Polyphasic study of wine *Lactobacillus* strains: taxonomic implications. *Int J Syst Evol Microbiol.* 2005, Vol. 55, No. 1, pages 197-207.

Dho, G., et al. Microbial characteristics of *Lactobacillus plantarum* P17630 contained in vaginal suppositories. *GIMMOC.* 2003, Vol. VII, No. 2, pages 102-108.

Owen, D. H. et al. A vaginal fluid simulant. Contraception. 1999, Vol. 59, No. 2, pages 91-95.

Ghosh, S. K., et al. Quantification of Human beta-Defensin-2 and -3 in Body Fluids: Application for Studies of Innate Immunity. *Clin Chem.* 2007, Vol. 53, No. 4, pages 757-765.

Archibald, F., Manganese: its acquisition by and function in the lactic acid bacteria. *Crit Rev Microbiol,* 1986, Vol. 13, No. 1, pages 63-109.

Atassi, F., et al. *Lactobacillus* strains isolated from the vaginal microbiota of healthy women inhibit *Prevotella bivia* and *Gardnerella vaginalis* in coculture and cell culture. *FEMS Immunology & Medical Microbiology.* 2006, Vol. 48, No. 3, pages 424-432.

Mastromarino, P., et al. Characterization and selection of vaginal *Lactobacillus* strains for the preparation of vaginal tablets. *Journal of Applied Microbiology.* 2002, Vol. 93, No. 5, pages 884-893.

Culici, M., et al. Adhesion of *Lactobacillus plantarum* P 17630 to vaginal epithelial cells and its influence on *Candida albicans* adhesion. *GIMMOC.* 2004, Vol. 8, No. 1, pages 34-41.

Saarela, M., et al. Stationary-phase acid and heat treatments for improvement of the viability of probiotic *lactobacilli* and bifidobacteria. *Journal of Applied Microbiology.* 2004, Vol. 96, No. 6, pages 1205-1214.

Jacques, M., et al. The normal microflora of the female rabbit's genital tract. *Can J Vet Res.* 1986, Vol. 50, pages 272-274.

Stapleton A. E, et al. Randomized, Placebo-Controlled Phase 2 Trial of a *Lactobacillus crispatus* Probiotic Given Intravaginally for Prevention of Recurrent Urinary Tract Infection, *Clinical Infectious Diseases.* 2011, Vol. 52, No. 10, pages 1212-1217.

EP 1436380 B1

---

The invention claimed is:

1. A method for the treatment of candidiasis comprising administering a subject in need thereof with an amount of a composition comprising a strain of *Lactobacillus pentosus* deposited in the Spanish Type Culture Collection under the accession number CECT 7504 effective for the treatment of candidiasis.

2. The method according to claim 1, wherein said candidiasis is vaginal candidiasis.

3. The method according to claim 2, wherein said vaginal candidiasis is caused by *Candida glabrata*.

4. The method according to claim 2, wherein said candidiasis is vaginal candidiasis with a high inflammatory response.

5. The method according to claim 1, wherein said method further comprises administering triazole antimycotic drugs or nystatin.

6. The method according to claim 1, wherein said candidiasis is oral or intestinal candidiasis.

7. A method for the treatment of bacterial vaginosis comprising administering to a subject in need thereof an amount of a composition comprising a strain of *Lactobacillus pentosus* deposited in the Spanish Type Culture Collection under the accession number CECT 7504 effective for the treatment of bacterial vaginosis.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="Forward primer for amplification"
      /organism="Artificial Sequence"

<400> SEQUENCE: 1
gagtttgatc ctggctcag                                               19

<210> SEQ ID NO 2
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Reverse primer for amplification"
      /organism="Artificial Sequence"

<400> SEQUENCE: 2
tacggytacc ttgttacgac tt                                           22
```

```
<210> SEQ ID NO 3
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Forward primer 27f for sequencing"
      /organism="Artificial Sequence"

<400> SEQUENCE: 3
agagtttgat cctggctcag                                              20

<210> SEQ ID NO 4
<211> LENGTH: 57
<212> TYPE: DNA
<213> ORGANISM: Artificial Sequence
<220> FEATURE:
<221> NAME/KEY: source
<222> LOCATION: 1..57
<223> OTHER INFORMATION: /mol_type="unassigned DNA"
      /note="Forward primer 357f for sequencing"
      /organism="Artificial Sequence"

<400> SEQUENCE: 4
cgcccgccgc gccccgcgcc cggcccgccg ccccgccc cctacgggag gcagcag      57

<210> SEQ ID NO 5
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Reverse primer 907r for sequencing"
      /organism="Artificial Sequence"

<400> SEQUENCE: 5
ccgtcaattc ctttgagttt                                              20

<210> SEQ ID NO 6
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="Reverse primer 1492r for sequencing"
      /organism="Artificial Sequence"

<400> SEQUENCE: 6
ggttaccttg ttacgactt                                               19

<210> SEQ ID NO 7
<211> LENGTH: 1384
<212> TYPE: DNA
<213> ORGANISM: Lactobacillus pentosus
<220> FEATURE:
<221> NAME/KEY: source
<222> LOCATION: 1..1384
<223> OTHER INFORMATION: /mol_type="unassigned DNA"
      /note="Sequence of the 16S gene of strain CECT 7504"
      /organism="Lactobacillus pentosus"

<400> SEQUENCE: 7
gattggtgct tgcatcatga tttacatttg agtgagtggc gaactggtga gtaacacgtg    60
```

-continued

```
ggaaacctgc ccagaagcgg gggataacac ctggaaacag atgctaatac cgcataacaa      120
cttggaccgc atggtccgag tttgaaagat ggcttcggct atcactttg gatggtcccg       180 cggcgtatta gctagatggt ggggtaacgg ctcaccatgg caatgatacg tagccgacct      240
gagagggtaa tcggccacat tgggactgag acacggccca aactcctacg ggaggcagca      300
gtagggaatc ttccacaatg gacgaaagtc tgatggagca acgccgcgtg agtgaagaag      360
ggtttcggct cgtaaaactc tgttgttaaa gaagaacata tctgagagta actgttcagg      420
tattgacggt atttaaccag aaagccacgg ctaactacgt gccagcagcc gcggtaatac      480
gtaggtggca agcgttgtcc ggatttattg ggcgtaaagc gagcgcaggc ggtttttta     540 gtctgatgtg aaagccttcg gctcaaccga agaagtgcat cggaaactgg gaaacttgag      600
tgcagaagag gacagtggaa ctccatgtgt agcggtgaaa tgcgtagata tatggaagaa      660
caccagtggc gaaggcggct gtctggtctg taactgacgc tgaggctcga agtatgggt       720 agcaaacagg attagatacc ctggtagtcc ataccgtaaa cgatgaatgc taagtgttgg     780
agggtttccg cccttcagtg ctgcagctaa cgcattaagc attccgcctg gggagtacgg      840
ccgcaaggct gaaactcaaa ggaattgacg ggggcccgca caagcggtgg agcatgtggt     900
ttaattcgaa gctacgcgaa gaaccttacc aggtcttgac atactatgca aatctaagag     960
attagacgtt cccttcgggg acatggatac aggtggtgca tggttgtcgt cagctcgtgt     1020
cgtgagatgt tgggttaagt cccgcaacga gcgcaaccct tattatcagt tgccagcatt     1080
aagttgggca ctctggtgag actgccggtg acaaaccgga ggaaggtggg gatgacgtca     1140
aatcatcatg ccccttatga cctgggctac acacgtgcta caatgggatgg tacaacgagt    1200 tgcgaactcg cgagagtaag ctaatctctt aaagccattc tcagttcgga ttgtaggctg     1260
caactcgcct acatgaagtc ggaatcgcta gtaatcgcgg atcagcatgc cgcggtgaat    1320
acgttcccgg gccttgtaca caccgcccgt cacaccatga gagtttgtaa cacccaaagt    1380
cggt                                                                 1384
```

<210> SEQ ID NO 8
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
    /note="Forward primer for real-time PCR quantification "
    /organism="Artificial Sequence"

<400> SEQUENCE: 8
tggatcacct cctttctaag gaat                                              24

<210> SEQ ID NO 9
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
    /note="Reverse primer for real-time PCR quantification "
    /organism="Artificial Sequence"

<400> SEQUENCE: 9
tgttctcggt ttcattatga aaaaata                                           27

```
<210> SEQ ID NO 10
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="Probe for real-time PCR quantification"
      /organism="Artificial Sequence"

<400> SEQUENCE: 10
acattcttcg aaactttgt                                                 19
```